(12) United States Patent
Chen et al.

(10) Patent No.: US 10,317,350 B2
(45) Date of Patent: Jun. 11, 2019

(54) ACTIVE, VARIABLE SAMPLE CONCENTRATION METHOD AND APPARATUS FOR SUB-PPB MEASUREMENTS AND EXEMPLARY X-RAY ANALYSIS APPLICATIONS THEREOF

(71) Applicant: X-RAY OPTICAL SYSTEMS, INC., East Greenbush, NY (US)

(72) Inventors: Zewu Chen, Schenectady, NY (US); George Allen, Middle Grove, NY (US); Andrew Hider, Saratoga Springs, NY (US); Danhong Li, Latham, NY (US); Jon Dunphy, East Greenbush, NY (US); Joseph Spinazola, Medway, MA (US)

(73) Assignee: X-RAY OPTICAL SYSTEMS, INC., East Greenbush, NY (US)

( * ) Notice: Subject to any disclaimer, the term of this patent is extended or adjusted under 35 U.S.C. 154(b) by 342 days.

(21) Appl. No.: 15/314,620

(22) PCT Filed: May 29, 2015

(86) PCT No.: PCT/US2015/033137
§ 371 (c)(1),
(2) Date: Nov. 29, 2016

(87) PCT Pub. No.: WO2015/184234
PCT Pub. Date: Dec. 3, 2015

(65) Prior Publication Data
US 2017/0097311 A1 Apr. 6, 2017

Related U.S. Application Data

(60) Provisional application No. 62/004,958, filed on May 30, 2014.

(51) Int. Cl.
*G01N 23/223* (2006.01)
*G01N 33/18* (2006.01)

(52) U.S. Cl.
CPC ....... *G01N 23/223* (2013.01); *G01N 33/1813* (2013.01); *G01N 2223/0766* (2013.01); *G01N 2223/315* (2013.01); *G01N 2223/652* (2013.01)

(58) Field of Classification Search
CPC .............. G01N 23/22; G01N 23/2202; G01N 23/2204; G01N 23/223; G01N 2223/076;
(Continued)

(56) References Cited

U.S. PATENT DOCUMENTS 3,761,225 A * 9/1973 Rasmussen .......... G01N 23/203
250/381
5,563,929 A 10/1996 Connolly et al.
(Continued)

FOREIGN PATENT DOCUMENTS

CN 1102881 A 5/1995
CN 102792157 A 11/2012
(Continued)

OTHER PUBLICATIONS

Tsuji et al., "Grazing-Exit and Micro X-Ray Fluorescence Analyses for Chemical Microchips", Analytical Sciences, vol. 21, No. 10, Jul. 10, 2005 (5 pages).
(Continued)

*Primary Examiner* — Thomas R Artman
(74) *Attorney, Agent, or Firm* — Kevin P. Radigan, Esq.; Heslin Rothenberg Farley & Mesiti P.C.

(57) ABSTRACT

A sample handling apparatus/technique/method for a material analyzer, which provides active, variable concentration of a sample, using a measurement marker introduced into the sample, to measurably concentrate an analyte in a liquid
(Continued)

(e.g., water) sample. Active, variable concentration allows otherwise lower level analytes to be concentrated in a measurable way. This enables measurements at higher (e.g., concentrated) levels, which can be extrapolated to obtain their lower, original levels based on the concentration level—measured using the introduced marker as a guide. The sample handling apparatus may be used in combination with an optic-enabled x-ray analyzer, the x-ray analyzer including an x-ray engine with an x-ray excitation path and an x-ray detection path, usable during both during the concentration and analyte measurement.

25 Claims, 7 Drawing Sheets

(58) Field of Classification Search
CPC ..... G01N 2223/0766; G01N 2223/635; G01N 2223/637; G01N 2223/652; G01N 33/1813
See application file for complete search history.

(56) References Cited

U.S. PATENT DOCUMENTS

| | | | |
|---|---|---|---|
| 6,801,595 B2 | 10/2004 | Grodzins et al. | |
| 6,821,434 B1 | 11/2004 | Moore et al. | |
| 7,016,462 B1* | 3/2006 | Keville | G01N 23/223 378/45 |
| 2005/0157843 A1 | 7/2005 | Chen et al. | |
| 2005/0157894 A1 | 7/2005 | Chen et al. | |
| 2013/0239666 A1 | 9/2013 | Carpenter et al. | |
| 2014/0011285 A1 | 1/2014 | Josse et al. | |
| 2014/0260561 A1* | 9/2014 | Brost | G01N 21/05 73/61.48 |
| 2016/0274042 A1* | 9/2016 | Chen | G01N 23/223 |
| 2017/0097311 A1* | 4/2017 | Chen | G01N 23/223 |

FOREIGN PATENT DOCUMENTS

| | | |
|---|---|---|
| EP | 2620507 A1 | 7/2013 |
| JP | H07-136401 A | 5/1995 |
| JP | 2010-261895 A | 11/2010 |

OTHER PUBLICATIONS

Dhara et al., "Energy Dispersive X-Ray Fluorescence Determination of Cadmium in Uranium Matrix Using Cd Kalpha Line Excited by Continuum", Spectrochimical Acta. Part B: Atomic Spectroscopy, vol. 65, No. 6, Jun. 2010 (5 pages).

Chen et al., International Search Report and Written Opinion issued in PCT/US2015/033137, dated Aug. 27, 2015 (9 pages).

* cited by examiner

ACTIVE, VARIABLE SAMPLE CONCENTRATION METHOD AND APPARATUS FOR SUB-PPB MEASUREMENTS AND EXEMPLARY X-RAY ANALYSIS APPLICATIONS THEREOF

CROSS-REFERENCE TO RELATED APPLICATION

This application claims the benefit of International Application No. PCT/US2015/033137, filed May 29, 2015, which was published Dec. 3, 2015, as PCT Publication No. WO 2015/184234 A1, and which claims the benefit of U.S. provisional patent application Ser. No. 62/004,958, filed May 30, 2014. Each of the above-noted applications is hereby incorporated herein by reference in its entirety.

TECHNICAL FIELD

This invention relates in general to apparatus and methods used for analysis of samples. More particularly, the present invention is directed to sample preparation using variable sample concentration for sub-ppb measurements.

BACKGROUND OF THE INVENTION

Trace element quantification at required detection limits can be very challenging. As one example, certain jurisdictions are moving to enforce environmental limits of 0.02-2 parts-per-million (ppm) for dangerous elements such as Cadmium in water streams, which is equivalent to 20-2000 parts-per-billion (ppb). The analytical performance goals placed on measurement technology to actually certify such low levels, often assessed using instrument level-of-detection (LOD), needs to be less than the regulated limit, possibly resulting in required LODs of less than one (1) ppb- or sub-ppb levels. The present invention is directed to reaching such limits using any type of measurement engine technology (X-RAY, ICP, AAS, MS, etc).

In one example of measurement technology, x-ray analysis is used across many test and monitoring applications such as environmental, consumer products, medical, pharmaceutical, and petroleum.

In one example of x-ray technology, x-ray fluorescence (XRF) is an analytical technique by which a substance is exposed to a beam of x-rays to determine, for example, the presence and concentrations of certain components. In XRF, at least some of the elemental constituents of the substance exposed to x-rays can absorb x-ray photons and produce characteristic secondary fluorescence. These secondary x-rays are characteristic of the elemental constituents in the substance. Upon appropriate detection and analysis these secondary x-rays can be used to characterize and/or quantify one or more of the elemental constituents in the sample.

Examples of XRF technology include U.S. Pat. Nos. 6,934,359 and 7,072,439, hereby incorporated by reference herein in their entirety and assigned to X-Ray Optical Systems, Inc., the assignee of the present invention. These patents disclose monochromatic wavelength dispersive x-ray fluorescence (MWD XRF) techniques and systems for the analysis of samples, e.g., trace level measurement of sulfur in petroleum products. U.S. Pat. No. 7,738,630, hereby incorporated by reference herein in its entirety and assigned to X-Ray Optical Systems, Inc., the assignee of the present invention, discloses monochromatic excitation, energy dispersive x-ray fluorescence (ME-EDXRF) techniques and systems for the analysis of samples, e.g., trace measurement of toxins in consumer products and other materials.

Many methods of analytical testing (including x-ray) take place off-line, i.e., using a bench-top, laboratory-type instrument to analyze a sample. The sample is removed from its environment (e.g., for fuel, from a refinery or transportation pipeline) and then deposited in a sample chamber; or into a windowed sample cell which is then deposited into a chamber. Off-line, bench-top instruments need not meet any unusual operational/pressure/environmental/size/weight/space/safety constraints, but merely need to provide the requisite measurement precision for a manually-placed sample. Moreover, off-line instruments can be easily maintained between measurements.

In contrast to off-line analysis, on-line analysis can provide "real-time" monitoring of sample composition at various points in a manufacturing process, a refinery, or in environmental stream handling. For example, all fuel products are subject to sulfur level compliance—requiring some variant of on-line monitoring during fuel refining and transportation in pipelines. On-line analysis, however, requires consideration of numerous operational issues not generally present in an off-line, laboratory setting. A fully automated sample handling system may be required—with little or no manual intervention or maintenance. Also, since fluids can be under varying pressure and flow in pipes or other channels, any sample handling system must account for pressure differentials.

What is required, therefore, to meet the challenges of such low detection levels, are improved techniques in sample handling, placement, x-ray excitation, and x-ray detection.

SUMMARY OF THE INVENTION

The shortcomings of the prior art are overcome and additional advantages are provided by the present invention which in one aspect is a technique for active, variable concentration of a sample having an analyte therein requiring measurement, using a measurement marker introduced into the sample, to measurably concentrate the analyte in the sample, wherein measurement at a higher (e.g., concentrated) analyte level is extrapolated to obtain its lower, original level based on a concentration factor measured using the introduced marker as a guide. X-ray analysis is one measurement technique that can be used, including but not limited to a monochromatic wavelength-enabled XRF analyzer; e.g., an MWDXRF or ME-EDXRF analyzer.

The present invention may include a method for concentration of a sample having a first analyte level therein requiring measurement in an analyzer, including concentrating the sample, and therefore the first analyte level in the sample; determining a concentration factor of the concentrated sample; measuring a second analyte level in the concentrated sample; and determining the first analyte level according to the measured, second analyte level and the concentration factor. This may also include combining a measurement marker and the sample; and measuring a level of the measurement marker in the concentrated sample, from which the concentration factor is determined.

The invention may further include measuring a volume of the measurement marker and sample to ensure an adequate level thereof for said measuring, including in one example repeatedly supplying sample to a sample area of the analyzer, to ensure the adequate level thereof.

The invention may further include controllably heating the sample to evaporate fluid therein to thereby concentrate the first analyte level in the sample.

The invention also includes an apparatus for concentration of a sample having a first analyte level therein requiring measurement, including: a sample platform for supporting a sample; a sample dispenser for dispensing the sample onto the holder; an element for concentrating the sample, and therefore the first analyte level in the sample; a measurement engine for measuring a second analyte level in the concentrated sample; and wherein the first analyte level is determined according to the measured, second analyte level and a concentration factor of the sample.

The invention may further include a measurement marker combining chamber for combining a measurement marker and the sample; wherein the measurement engine measures a level of the measurement marker in the concentrated sample, from which the concentration factor is determined.

The measurement engine may measure a volume of the measurement marker and sample to ensure an adequate level thereof while concentrating the sample.

The sample may be concentrated by repeatedly supplying sample to the sample platform, to ensure the adequate level thereof.

A heating element may be provided for controllably heating the sample to evaporate fluid therein to thereby concentrate the first analyte level in the sample.

The methods, techniques, and apparatus of the present invention may be used in combination with an x-ray analyzer, the x-ray analyzer including the measurement engine comprising: an x-ray excitation path; and an x-ray detection path; wherein the x-ray excitation and/or the x-ray detection paths define an x-ray analysis focal area for said measuring.

The focal area may be defined by focused x-rays to/from at least one focusing optic in the x-ray excitation path and/or the x-ray detection path.

The focusing optic may be at least one curved diffracting optic or a polycapillary optic; e.g., a focusing monochromatic optic, e.g., a curved crystal optic or curved multi-layer optic. At least one focusing optic in the x-ray detection path may be positioned such that an input focal point thereof is at the x-ray focal area, and corresponds to an output focal point of at least one focusing optic in the x-ray excitation path.

The measurement engine of the x-ray analyzer may be a monochromatic wavelength-enabled XRF analyzer, or an MWDXRF or ME-EDXRF analyzer.

The sample may be primarily water, and the analyte measured may be cadmium, or any other analyte(s) of interest including but not limited to S, Cl, P, K, Ca, V, Mn, Fe, Co, Ni, Cu, Zn, Hg, As, Pb, and/or Se Further, additional features and advantages are realized by the techniques of the present invention. Other embodiments and aspects of the invention are described in detail herein and are considered a part of the claimed invention.

BRIEF DESCRIPTION OF THE DRAWINGS

The subject matter regarded as the invention is particularly pointed out and distinctly claimed in the claims at the conclusion of the specification. The foregoing and other objects, features, and advantages of the invention are apparent from the following detailed description taken in combination with the accompanying drawings in which:

DETAILED DESCRIPTION OF THE INVENTION

As discussed above, measurement techniques of various types are being called upon to perform at very low LODs, including sub-ppb levels. The present invention is directed to active, variable concentration of the sample, in one embodiment using a measurement marker introduced into the sample, to measurably concentrate an analyte in a liquid (e.g., water) sample. Active, variable concentration in accordance with the present invention allows otherwise lower level analytes to be concentrated in a measurable way. This enables measurements at higher (e.g., concentrated) levels, which can be extrapolated to obtain their lower, original levels based on the concentration level—measured using the introduced marker as a guide. This technique is applicable to any analytical measurement technique.

Figure 1:
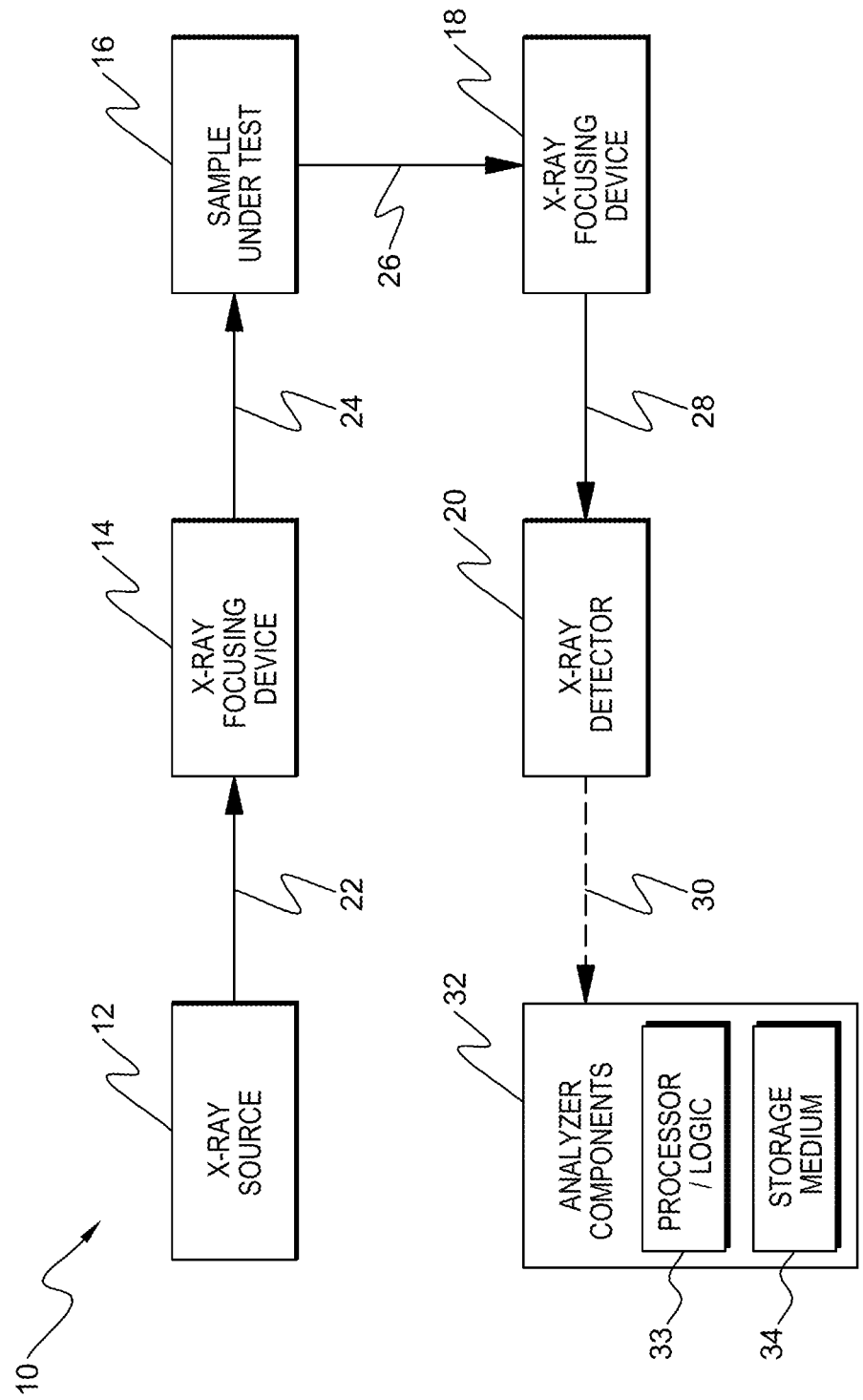
FIG. 1 is a functional block diagram of the elements of an exemplary x-ray fluorescence system.

Optic-enabled XRF is discussed below as one example of an analytical technique usable with the present invention. FIG. 1 is a high level, functional block diagram of an exemplary XRF system or analyzer 10 used for exposing a sample to x-ray radiation to produce fluorescent radiation which can then be detected and analyzed to determine a characteristic of the sample. The analyzer may include an x-ray source 12, a first x-ray focusing device 14, a sample under test 16, a second x-ray focusing device 18, an x-ray detector 20, and an analyzer components 32 for providing the analytical result. The x-ray source 12, for example, an x-ray tube, produces a beam of x-rays 22. Beam 22 may diffracted or focused by one or more x-ray focusing optics 14 as discussed further below.

When irradiated by beam 24, at least one of the constituents of sample in chamber 16 is excited in such a fashion that the constituent fluoresces, that is, produces a secondary source of x-rays 26 due to excitation by x-rays 24. Again, since x-ray beam 26 is typically a diverging beam of x-rays, beam 26 may be focused by optional second x-ray focusing optics 18, for example, to produce a focused beam of x-rays 28 directed toward x-ray detector 20.

X-ray detector 20 may be a proportional counter-type or a semiconductor type x-ray detector (e.g., silicon drift detector), or any other suitable type of x-ray fluorescence detector known to one skilled in the art. Typically, x-ray detector 20 produces an electrical signal 30 containing a characteristic of the detected x-rays which is forwarded to analyzer components 32 for analysis, printout, or other display. Analyzer components 32 may include a computer program product including, for instance, one or more non-transitory computer readable storage media 34 to store computer readable program code means or processor/logic 33 thereon to provide and facilitate one or more aspects of the present invention.

X-ray focusing devices/optics 14, 18 for advanced XRF analyzers, including those below, may include, for example, curved crystal monochromating optics such as those disclosed in commonly assigned U.S. Pat. Nos. 6,285,506; 6,317,483; 7,035,374; 7,738,629; and PCT Publication WO2013/063253A1; and/or polycapillary optics such as those disclosed in commonly assigned U.S. Pat. Nos. 5,192, 869; 5,175,755; 5,497,008; 5,745,547; 5,570,408; and 5,604,353. Optic/source combinations such as those disclosed in commonly assigned U.S. Pat. Nos. 7,110,506; 7,209,545; and 7,257,193 are also useable. Each of the above-noted patents is hereby incorporated herein by reference in its entirety.

The following are two examples of x-ray-optic-enabled analyzer engines which may be used in connection with the present invention:

Exemplary MWD XRF X-Ray Analysis Engines:

The assignee of the present invention has previously disclosed a Monochromatic Wavelength Dispersive X-Ray Fluorescence (MWD XRF) analyzer engine 120 using two monochromating optic sets (U.S. Pat. Nos. 6,934,359 and 7,072,439—hereby incorporated by reference herein in their entirety), as shown schematically in FIG. 2. The related SINDIE (Sulfur IN DIEsel) and CLORA (chlorine) product lines for the measurement of e.g., sulfur and chlorine in diesel fuel and other petroleum products revolutionized XRF and provide many advantages including: (1) signal/background (S/B) is improved due to monochromatic excitation of the sample by DCC1 14', i.e., the bremsstrahlung photons with energies under fluorescence peaks (which normally swamp these peaks of interest) can only reach the detector through scattering, therefore improving the S/B ratio dramatically compared to polychromatic excitation; (2) superior energy resolution—this eliminates all common interference problems and provides the physical basis for upstream applications; (3) inherent robustness and low maintenance—the analysis engine is low power, compact, with no moving parts or consumable gasses; and (4) unprecedented dynamic range, e.g., a quantification level from 0.3 ppm to 5% of sulfur in a sample.

Figure 2:
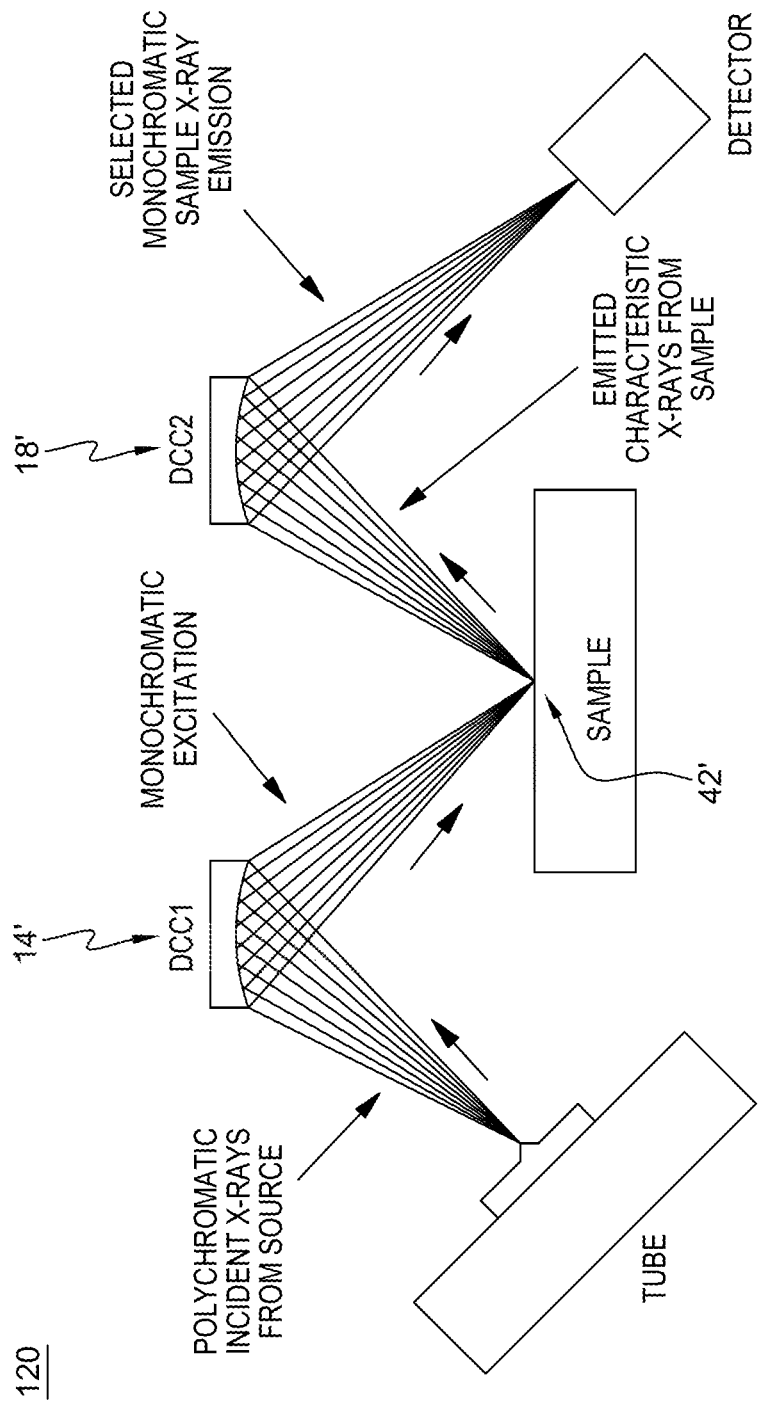
FIG. 2 is a schematic view of an exemplary MWD XRF x-ray engine useable with the sample handling apparatus of the present invention.

The MWD XRF engine 120, shown schematically in FIG. 2, includes curved monochromating optics 14' and 18' in the excitation and detection paths respectively, forming focal area or point 42' on the sample (discussed further below), which is the configuration of the SINDIE sulfur analyzer discussed above. However, an optic may only be present in one of these paths. In one example, an optic of any of the above-describe types may only be present in the excitation path, and the detection path would include an energy dispersive detector. This is the common configuration of an energy dispersive x-ray fluorescence (EDXRF) system, discussed further below.

Figure 3:
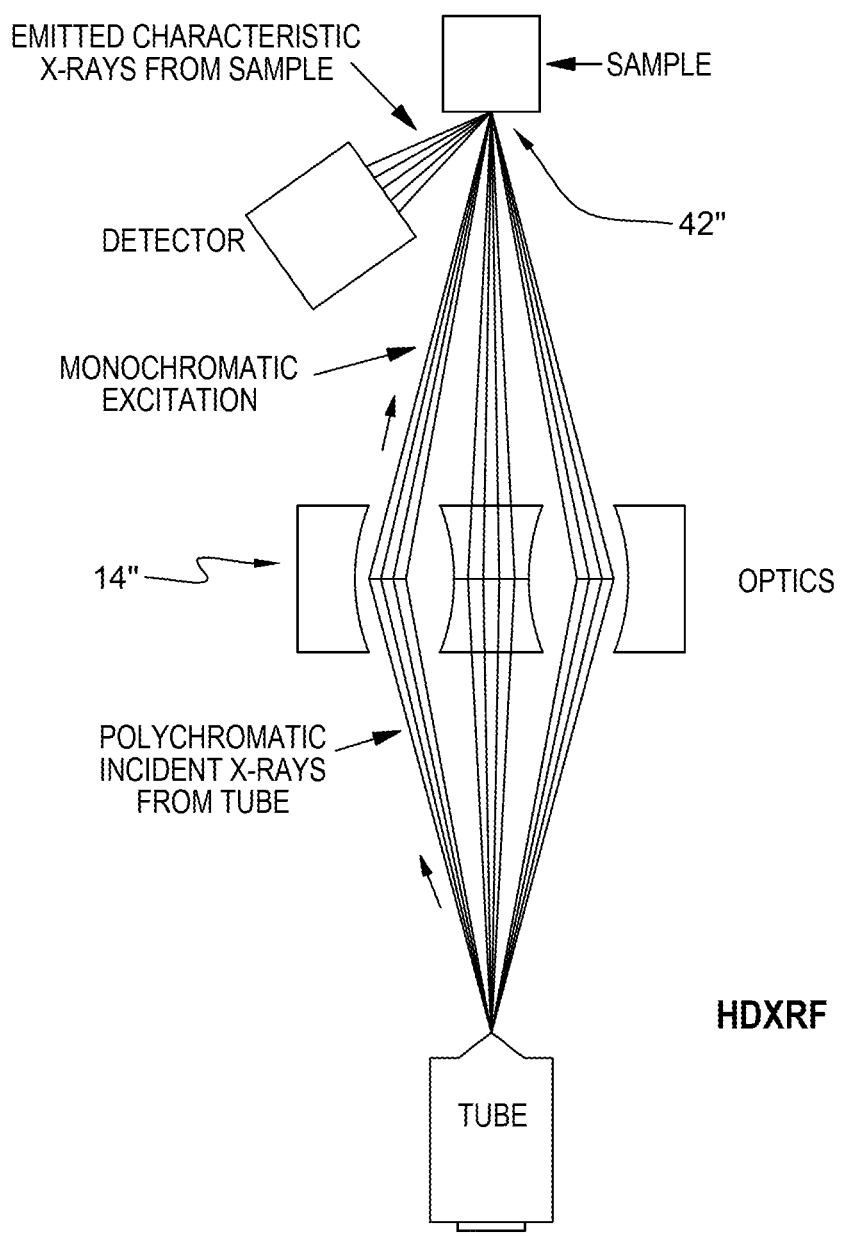
FIG. 3 is a schematic view of an exemplary ME EDXRF x-ray engine useable with the sample handling apparatus of the present invention.

Exemplary ME EDXRF X-Ray Analysis Engine:

Monochromatic Excitation, Energy Dispersive X-Ray Fluorescence (ME-EDXRF) analyzers can also be used for this application, in accordance with the present invention. The engine technology is disclosed in, e.g., U.S. Pat. No. 6,934,359 entitled XRF System Having Multiple Excitation Energy Bands In Highly Aligned Package, the entirety of which is hereby incorporated by reference herein. In one embodiment this engine 130 involves monochromatic excitation known as HD XRF as depicted schematically in FIG. 3. HD XRF is a multi-element analysis technique offering significantly enhanced detection performance over traditional ED or WD XRF. This technique applies state-of-the-art monochromating and focusing optics 14" illuminating a focal area or point 42" on the sample, enabling multiple select-energy excitation beams that efficiently excite a broad range of target elements in the sample. Monochromatic excitation dramatically reduces scattering background under the fluorescence peaks, greatly enhancing elemental detection limits and precision.

Figure 4A:
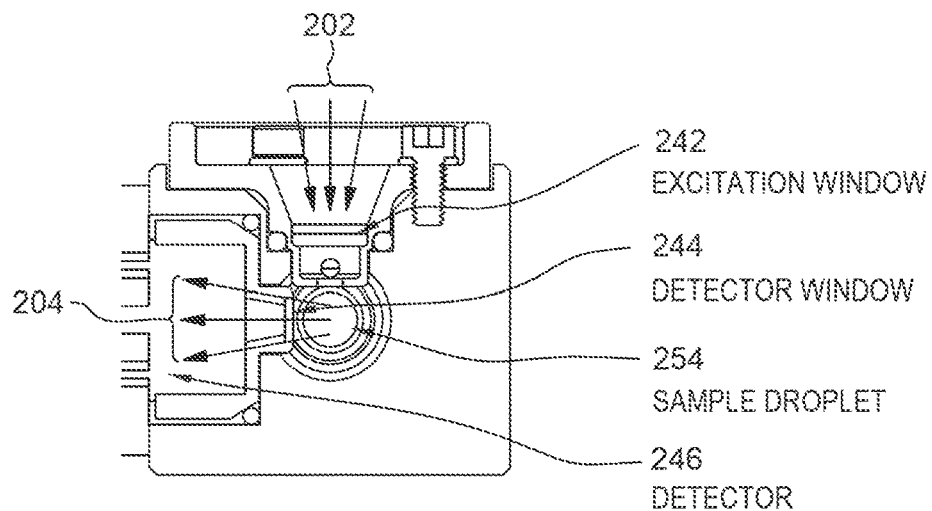
FIGS. 4a-4b are sectional views of an exemplary sample chamber for variable sample concentration, in accordance with one aspect of the present invention.
Figure 4B:
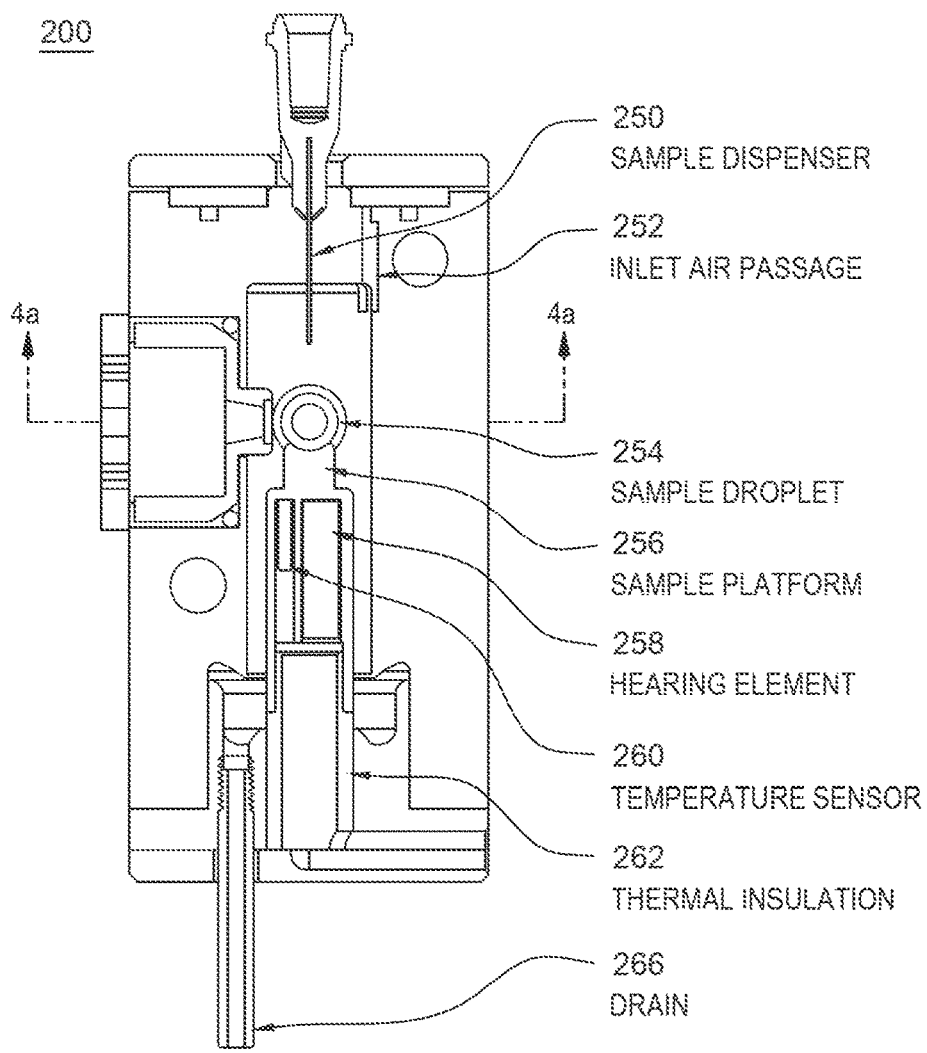

FIGS. 4a-4b are sectional views of an exemplary sample chamber 200 in accordance with one exemplary aspect of the present invention.

According to the present invention, the sample chamber 200 primarily functions to prepare and present a sample droplet 254 having an analyte-of interest therein to an analysis engine (e.g., x-ray, or any other type of engine), and to direct the used sampling materials to waste handling equipment. One exemplary measurement is for trace Cadmium levels in effluent waters, at potentially sub-ppb levels.

The sample chamber can be implemented as an online system expected to run autonomously for long periods of time, only interrupted for scheduled maintenance and cleaning in the case that self contamination levels have exceeded predetermined level; or alternatively in an off-line mode with static sample sets to analyze. Self contamination level sensing and self cleaning features may also form part of the present invention. In such an application, an entire measurement system (not shown) including sample chamber 200 can be typically installed with or without other instruments (usually pH, flow meter) to monitor the effluent from industrial sites or waste water treatment plants in a very autonomous manner. Plant personnel need not touch the instruments and may know little or nothing about the instrument. Off-line, bench-top implementations are also possible for interactive laboratory use for static sample sets.

The sample chamber provides active, variable concentration of the sample, in one embodiment using a measurement marker introduced into the sample, to measurably concentrate an analyte in a liquid (e.g., water) sample. Active, variable concentration in accordance with the present invention allows otherwise lower level analytes to be concentrated in a measurable way. This enables measurements at higher (e.g., concentrated) levels, which can be extrapolated to obtain their lower, original levels based on the concentration level—measured using the introduced marker as a guide.

With reference to FIG. 4, in accordance with the present invention, sample dispenser 250 "drops" or otherwise presents a fluid sample toward sample platform 254. Sample platform may be heated with a heating element 258, and its temperature monitored using temperature sensor 260. Active, controllable heating of the platform 256 (which itself may be insulated from the surrounding structures by air and/or thermal insulation 262) using heating element 258 and sensor 260 can be used to variably and controllably evaporate excess water in the sample droplet 254 supported on platform 256, while leaving the analyte (and potential marker element) concentrated in the remaining droplet for analysis by an analytical engine. In an x-ray analysis example (for example in accordance with the x-ray techniques discussed above with reference to FIGS. 1-3), excitation x-rays 242 are introduced through an excitation window 244, excite the sample droplet 254, producing fluorescence 204 toward a detector 246 which can be used to determine the concentration of the analyte, and marker if applicable, remaining in the residual sample droplet 254. As discussed further below, inlet air passage 252 and drain 266 are used to assist with the introduction and removal of sample, which may all be variably controlled using the exemplary fluidics of FIG. 5 and control system of FIG. 6, in accordance with exemplary aspects of the present invention.

The marker material (combined with sample in mixing or combining chamber 320) is chosen e.g., to be detectable during the concentrating by the measurement engine technology, non-interfering with the analyte of interest, readily available, disposable, etc. In the x-ray measurement engine example of the present invention, strontium meets various of these criteria and is therefore discussed herein. Other marker materials may be used, chosen according to these criteria.

Figure 5:
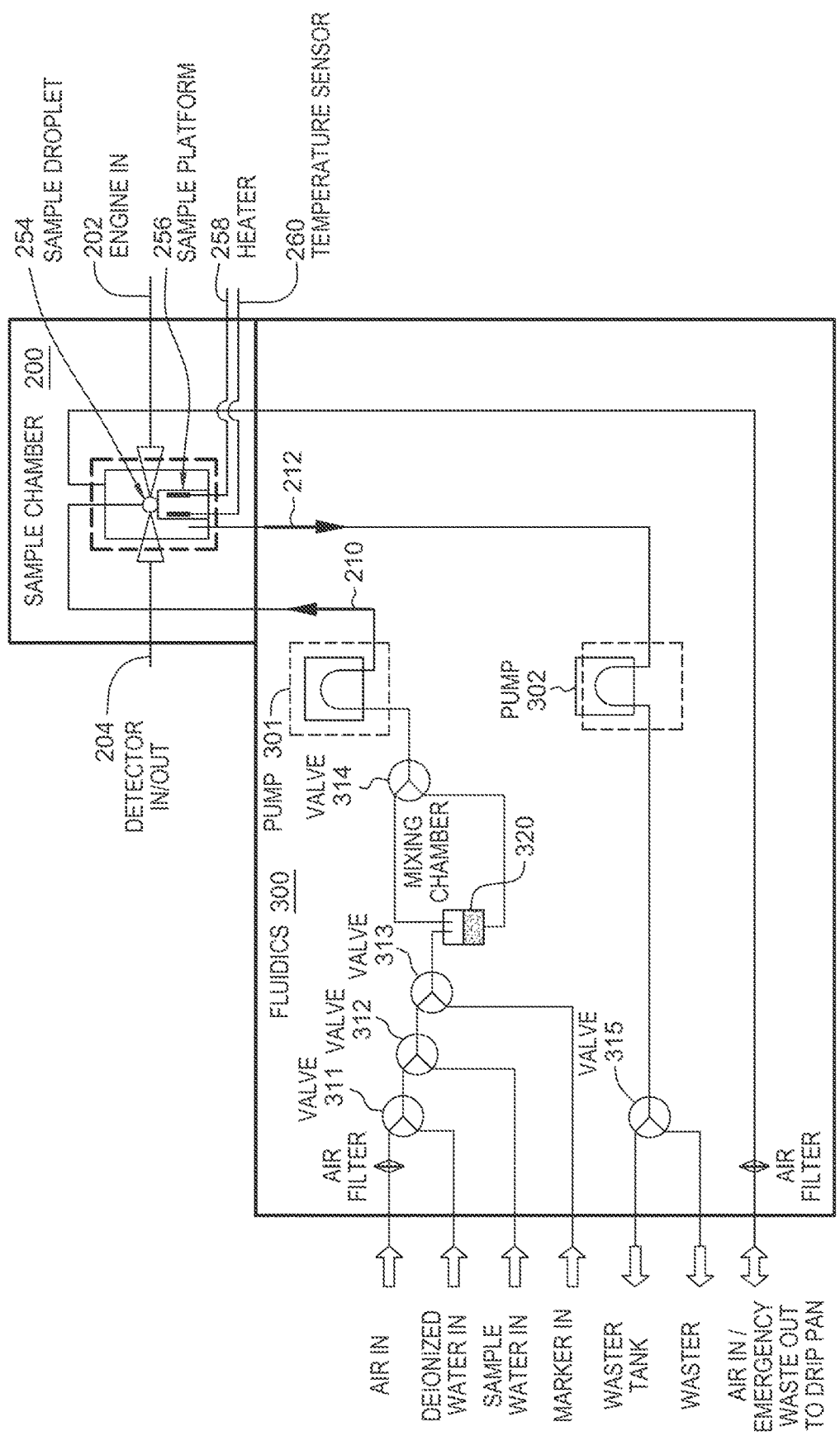
FIG. 5 is a schematic view of exemplary fluidics in accordance with one aspect of the present invention.

FIG. 5 is a schematic view of exemplary fluidic system 300 in accordance with one exemplary aspect of the present invention (where like reference numerals are used to denote like elements). The components of this system may be controllable to move sample into (210) for analysis, and out of (212) sample chamber 200, as follows:

Pump 301—delivers sample flow to sample chamber 200.
Pump 302—draws used sample from sample cell 200.
Valve 311—Off delivers air; on delivers deionized water.
Valve 312—Off delivers resolute from valve 311; on delivers sample.
Valve 313—Off delivers from resolute from valve 312; on delivers marker (e.g. strontium).
Valve 314—Off provides suction to prime mixing or combining chamber 320 (reverse these and scrub no/nc to minimize duty cycles); on delivers solution from mixing or combining chamber 320.
Valve 315—Off delivers waste from sample chamber 200 (via pump 302) to waster tank; on delivers waste from sample cell (via pump 302) to waster.

Any or all of the components of FIG. 5 may be controllable (implemented in e.g., analyzer components 32 of FIG. 1) to effect proper sample flow, marker flow, heat application (via heater 258) to provide active, variable concentration of the sample, in one embodiment using a measurement marker introduced into the sample, to controllably and measurably concentrate an analyte in a liquid (e.g., water) sample, for analysis in sample chamber 200.

Figure 6:
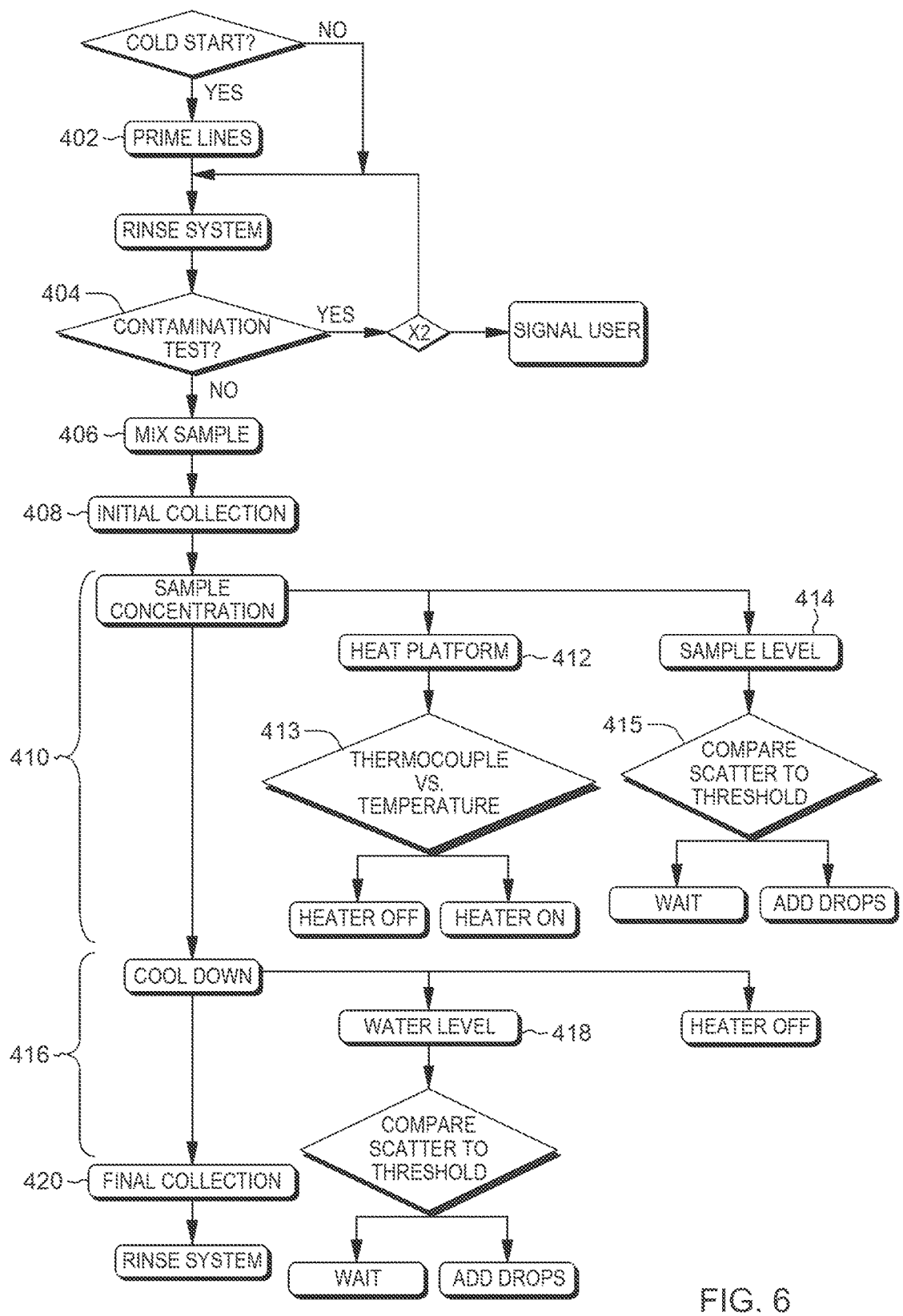
FIG. 6 is an exemplary flowchart depicting exemplary steps for carrying out the present invention.

FIG. 6 is a flowchart depicting exemplary steps for carrying out one exemplary aspect of the present invention (where like reference numerals are used to denote like elements). These steps can be performed in hardware, software, or a combination of both (implemented in e.g., analyzer components 32 of FIG. 1), and in connection with the controllable elements of FIGS. 4a-b (sample chamber) and FIG. 5 (fluidics), as follows:

Prime Lines 402—draws in a marker (e.g., strontium) and sample with analyte up to each respective valve in any desired sequence or combination thereof;
Contamination Test 404—uses distilled water from rinsing the system to run a background collection and determine if the system has been contaminated with either strontium or analyte (e.g., cadmium). This background collection can be advantageously performed using the measurement engine (e.g., x-ray) to determine if any undesired contaminants are present the system—by comparing an XRF measurement in step 404 to a desired, predetermined background level. Any anomalies in the measurement can be used to trigger additional rinses or service, as required (e.g., signal user as shown).
Mix Sample 406—fills the mixing or combining chamber 320 with sample and marker in any desired sequence or combination thereof, to produce (for example) a predetermined level of the strontium marker per volume unit of sample, in either absolute or relative terms, and inject into sample chamber 200.

Initial Collection 408—evaluates initial concentration of marker using measurement (e.g., x-ray) of the marker/sample combination now injected into chamber 200 (explained further below regarding FIG. 7). The peak of the marker is determined, so that a concentration factor can be established (e.g., 10×, 20×) for the next step—Sample Concentration 410.

Sample Concentration 410—variably controls heating element 258 to maintain an elevated temperature to facilitate a desired amount of evaporation of the sample. This may include the step Heats Stand 412 to a desired level using heating element 258 and temperature sensor/thermocouple 260 (discussed above) in step 413; and step Sample Level 414 which advantageously uses x-ray scatter feedback (e.g., from a scatter channel) to determine the sample droplet size itself—i.e., the amount of sample on the sample platform 256. Scatter is compared to a threshold level 415 to start adding sample when the level reaches a low threshold and continue until a desired threshold has been reached. This will repeat until the sample stand has been refilled a number of times (e.g., 20 in this example).

Cool Down 416—the sample is allowed to controllably cool to reach a steady volume for a predetermined, desired period of time to allow for analyte measurement; and if Water Level 418 (if scatter level indicates), additional water can be added to achieve the desired volume.

Final Collection 420—evaluates final concentration of marker and analyte in sample using XRF analysis, or other measurement technique in sample chamber 200. This measurement, potentially at sub-ppb levels, is extrapolated to an actual concentration of the analyte (e.g., cadmium) based upon the identified concentration of the marker, which was increased by the concentration factor (CF) achieved in Step 410 (Sample Concentration).

Figure 7:
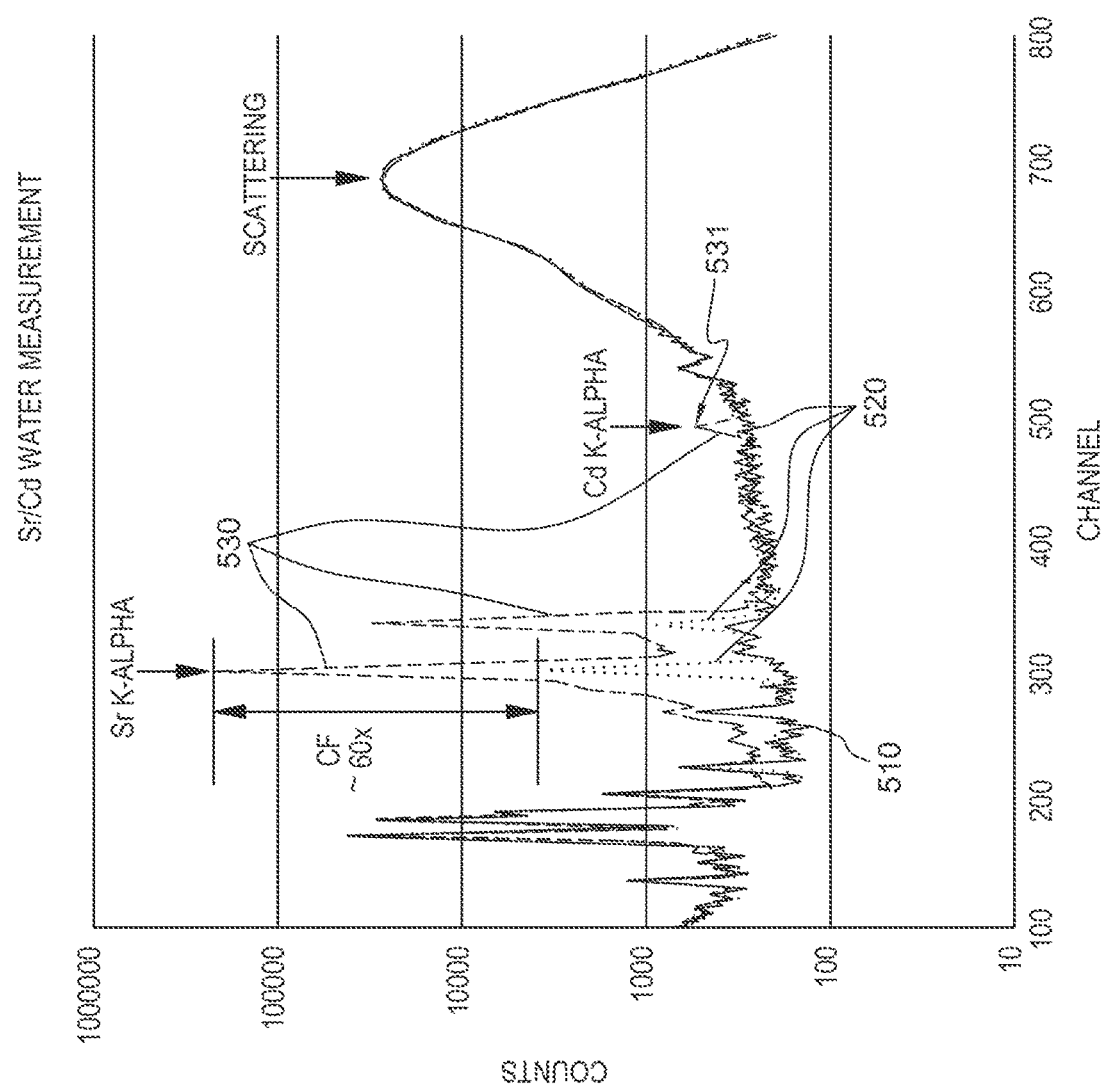
FIG. 7 is a spectral plot showing measurement of a marker and analyte of interest, before and after the active, variable sample concentration of the present invention.

FIG. 7 is a spectral graph showing measurement of a marker and analyte of interest, before and after the active, variable sample concentration of the present invention. Assuming that cadmium (Cd) is the analyte of interest in the sample (near detector channel 500 along the horizontal axis), plot line 510 shows a typical background measurement level. Plot line 520 shows an initial collection measurement (step 408) of the sample before its active concentration (step 410), obtained after adding marker (step 406), yet showing no discernable peak for Cd based on its low concentration in the sample at that point. Plot line 530 shows a final collection measurement (step 420) of the sample after its active concentration, now showing a discernible Cd peak level 531. This resultant Cd peak level 531 in the concentrated sample, now discernable, can be used to determine the actual (much lower) Cd concentration present in the original, pre-concentrated sample according to the sample concentration factor (CF) achieved in step 410. The actual Cd present in the sample is determined by dividing the measured Cd level of the concentrated sample by the concentration factor (CF).

This sample concentration factor (CF) is determined by measuring the relative marker peaks between plot lines 520 (pre-concentration) and 530 (post-concentration). In the example shown, CF is approximately 60×.

Other exemplary analytes measured in accordance with the present invention include: S, Cl, P, K, Ca, V, Mn, Fe, Co, Ni, Cu, Zn, Hg, As, Pb, and/or Se. Any other elements having unique signatures can also be measured according to the principles of the present invention.

The present invention provides active, variable concentration of the sample, in one embodiment using a measurement marker introduced into the sample, to measurably concentrate an analyte in a liquid (e.g., water) sample.

Active, variable concentration in accordance with the present invention allows otherwise lower level analytes to be concentrated in a measurable way. This enables measurements at higher (e.g., concentrated) levels, which can be extrapolated to obtain their lower, original levels based on the concentration level—measured using the introduced marker as a guide.

As will be appreciated by one skilled in the art, one or more aspects of the present invention may be embodied as a system, method or computer program product. Accordingly, one or more aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," "analyzer" or "system". Furthermore, one or more aspects of the present invention may take the form of a computer program product embodied in one or more computer readable medium(s) having computer readable program code embodied thereon.

Any combination of one or more computer readable medium(s) may be utilized. The computer readable medium may be a computer readable storage medium. A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Referring back to FIG. 1, in one example, analyzer 32 may include a computer program product including, for instance, one or more non-transitory computer readable storage media 34 to store computer readable program code means or processor/logic 33 thereon to provide and facilitate one or more aspects of the present invention.

Program code embodied on a computer readable medium may be transmitted using an appropriate medium, including but not limited to, wireless, wireline, optical fiber cable, RF, etc., or any suitable combination of the foregoing.

Computer program code for carrying out operations for one or more aspects of the present invention may be written in any combination of one or more programming languages, including an object oriented programming language, such as Java, Smalltalk, C++ or the like, and conventional procedural programming languages, such as the "C" programming language, assembler or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

One or more aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of one or more aspects of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In addition to the above, one or more aspects of the present invention may be provided, offered, deployed, managed, serviced, etc. by a service provider who offers management of customer environments. For instance, the service provider can create, maintain, support, etc. computer code and/or a computer infrastructure that performs one or more aspects of the present invention for one or more customers. In return, the service provider may receive payment from the customer under a subscription and/or fee agreement, as examples. Additionally or alternatively, the service provider may receive payment from the sale of advertising content to one or more third parties.

In one aspect of the present invention, an application may be deployed for performing one or more aspects of the present invention. As one example, the deploying of an application comprises providing computer infrastructure operable to perform one or more aspects of the present invention.

As a further aspect of the present invention, a computing infrastructure may be deployed comprising integrating computer readable code into a computing system, in which the code in combination with the computing system is capable of performing one or more aspects of the present invention.

As yet a further aspect of the present invention, a process for integrating computing infrastructure comprising integrating computer readable code into a computer system may be provided. The computer system comprises a computer readable medium, in which the computer medium comprises one or more aspects of the present invention. The code in combination with the computer system is capable of performing one or more aspects of the present invention.

Although various embodiments are described above, these are only examples. Further, other types of computing environments can benefit from one or more aspects of the present invention.

As a further example, a data processing system suitable for storing and/or executing program code is usable that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the invention for various embodiments with various modifications as are suited to the particular use contemplated.

What is claimed is:

1. A method for concentration of a sample having a first analyte level therein requiring measurement in an analyzer, comprising:
   concentrating the sample, and therefore the first analyte level in the sample;
   determining a concentration factor of the concentrated sample;
   measuring a second analyte level in the concentrated sample; and
   determining the first analyte level according to the measured, second analyte level and the concentration factor.

2. The method of claim 1, further comprising:
   combining a measurement marker and the sample;
   measuring a level of the measurement marker in the concentrated sample, from which the concentration factor is determined.

3. The method of claim 2, wherein said concentrating includes measuring a volume of the measurement marker and sample to ensure an adequate level thereof for said measuring.

4. The method of claim 3, wherein said concentrating includes repeatedly supplying sample to a sample area of the analyzer, to ensure the adequate level thereof.

5. The method of claim 1, wherein said concentrating includes controllably heating the sample to evaporate fluid therein to thereby concentrate the first analyte level in the sample.

6. The method of claim 1, further comprising using an x-ray analyzer, the x-ray analyzer including:
   an x-ray excitation path; and
   an x-ray detection path;
   wherein the x-ray excitation and/or the x-ray detection paths define an x-ray analysis focal area for said measuring.

7. The method of claim 6, wherein the focal area is defined by focused x-rays to/from at least one focusing optic in the x-ray excitation path and/or the x-ray detection path.

8. The method of claim 7, wherein the at least one focusing optic is at least one curved diffracting optic or a polycapillary optic.

9. The method of claim 8, wherein the at least one focusing optic is at least one focusing monochromatic optic.

10. The method of claim 9, wherein the at least one focusing monochromatic optic is a curved crystal optic or curved multi-layer optic.

11. The method of claim 7, wherein at least one focusing optic in the x-ray detection path is positioned such that an input focal point thereof is at the x-ray focal area, and corresponds to an output focal point of at least one focusing optic in the x-ray excitation path.

12. The method of claim 6, wherein the x-ray analyzer comprises a monochromatic wavelength-enabled XRF analyzer, or an MWDXRF or ME-EDXRF analyzer.

13. The method of claim 1, wherein the sample is primarily water, and the analyte measured is cadmium.

14. An apparatus for concentration of a sample having a first analyte level therein requiring measurement, comprising:
- a sample platform for supporting a sample;
- a sample dispenser for dispensing the sample onto the holder;
- an element for concentrating the sample, and therefore the first analyte level in the sample;
- a measurement engine for measuring a second analyte level in the concentrated sample; and
- wherein the first analyte level is determined according to the measured, second analyte level and a concentration factor of the sample.

15. The apparatus of claim 14, further comprising:
- a measurement marker combining chamber for combining a measurement marker and the sample;
- wherein the measurement engine measures a level of the measurement marker in the concentrated sample, from which the concentration factor is determined.

16. The apparatus of claim 15, wherein the measurement engine measures a volume of the measurement marker and sample to ensure an adequate level thereof while concentrating the sample.

17. The apparatus of claim 16, wherein the sample is concentrated by repeatedly supplying sample to the sample platform, to ensure the adequate level thereof.

18. The apparatus of claim 14, further comprising a heating element for controllably heating the sample to evaporate fluid therein to thereby concentrate the first analyte level in the sample.

19. The apparatus of claim 14, in combination with an x-ray analyzer, the x-ray analyzer including the measurement engine comprising:
- an x-ray excitation path; and
- an x-ray detection path;
- wherein the x-ray excitation and/or the x-ray detection paths define an x-ray analysis focal area for measuring the sample.

20. The combination of claim 19, wherein the focal area is defined by focused x-rays to/from at least one focusing optic in the x-ray excitation path and/or the x-ray detection path.

21. The combination of claim 20, wherein the at least one focusing optic is at least one curved diffracting optic or a polycapillary optic.

22. The combination of claim 21, wherein the at least one focusing optic is at least one focusing monochromatic optic.

23. The combination of claim 22, wherein the at least one focusing monochromatic optic is a curved crystal optic or curved multi-layer optic.

24. The combination of claim 23, wherein at least one focusing optic in the x-ray detection path is positioned such that an input focal point thereof is at the x-ray focal area, and corresponds to an output focal point of at least one focusing optic in the x-ray excitation path.

25. The combination of claim 19, wherein the measurement engine of the x-ray analyzer comprises a monochromatic wavelength-enabled XRF analyzer, or an MWDXRF or ME-EDXRF analyzer.

* * * * *